United States Patent
Liao

(10) Patent No.: US 10,123,997 B2
(45) Date of Patent: Nov. 13, 2018

(54) TARGET FOR TREATING HEPATITIS B VIRUS

(71) Applicant: Yong Liao, Chongqing (CN)

(72) Inventor: Yong Liao, Chongqing (CN)

(*) Notice: Subject to any disclaimer, the term of this patent is extended or adjusted under 35 U.S.C. 154(b) by 0 days.

(21) Appl. No.: 15/571,154

(22) PCT Filed: Jun. 15, 2015

(86) PCT No.: PCT/CN2015/081467
§ 371 (c)(1),
(2) Date: Nov. 1, 2017

(87) PCT Pub. No.: WO2016/201605
PCT Pub. Date: Dec. 22, 2016

(65) Prior Publication Data
US 2018/0256550 A1    Sep. 13, 2018

(51) Int. Cl.
| | | |
|---|---|---|
| *A61K 31/519* | (2006.01) | |
| *A61K 31/436* | (2006.01) | |
| *A61P 31/20* | (2006.01) | |
| *A61K 31/4985* | (2006.01) | |
| *A61K 38/17* | (2006.01) | |
| *A61K 31/365* | (2006.01) | |
| *C07K 14/47* | (2006.01) | |

(52) U.S. Cl.
CPC .......... *A61K 31/436* (2013.01); *A61K 31/365* (2013.01); *A61K 31/4985* (2013.01); *A61K 31/519* (2013.01); *A61K 38/17* (2013.01); *A61P 31/20* (2018.01); *C07K 14/47* (2013.01)

(58) Field of Classification Search
None
See application file for complete search history.

(56) References Cited

U.S. PATENT DOCUMENTS

| | | | | |
|---|---|---|---|---|
| 2009/0221633 A1* | 9/2009 | Joseph | ............... | C07D 217/02 514/307 |
| 2011/0178076 A1* | 7/2011 | Huber | ............... | A61K 31/4745 514/229.8 |
| 2014/0370059 A1* | 12/2014 | Ahmed | ............. | A61K 31/4745 424/277.1 |

FOREIGN PATENT DOCUMENTS

| | | |
|---|---|---|
| CN | 101466683 A | 6/2009 |
| CN | 103732226 A | 4/2014 |

OTHER PUBLICATIONS

Davies et al. (Mol Cancer Ther; 11(4): 873-87, 2012).*
Wu, Xiangqin; "Phosphorylation Akt Regulate Autophagy and the C77 of Fungi Secondary Metabolites Affect Autophagy and HBV Replication", Master's Dissertation of Anhui University, Dec. 31, 2014 (Dec. 31, 2014), p. 42.

* cited by examiner

*Primary Examiner* — Bong-Sook Baek
(74) *Attorney, Agent, or Firm* — SZDC Law P.C.

(57) ABSTRACT

A method of treating hepatitis B virus includes inhibiting the activities of AKT and/or mTOR, inhibiting the synthesis of 5-phosphate ribose, and inhibiting HBV DNA and HBV cccDNA.

2 Claims, 6 Drawing Sheets

Specification includes a Sequence Listing.

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: DNA Sequence of primer P1

<400> SEQUENCE: 1
ctgaatcctg cggacgaccc                                                    20

<210> SEQ ID NO 2
<211> LENGTH: 18
<212> TYPE: DNA
<213> ORGANISM: Artificial Sequence
<220> FEATURE:
<223> OTHER INFORMATION: DNA Sequence of primer P2

<400> SEQUENCE: 2
gccccaaagc cacccaag                                                      18

TARGET FOR TREATING HEPATITIS B VIRUS

This application is a national stage application of PCT/CN2015/081467, filed on Jun. 15, 2015, which is incorporated by reference for all purposes as if fully set forth herein.

FIELD OF THE INVENTION

The present invention relates to a target against hepatitis B virus, in particular, to the use of AKT and mTOR as drug targets in anti-HBV therapy.

BACKGROUND OF THE INVENTION

HBV (Hepatitis B Virus) has seriously endangered human health, causing huge economic and mental burdens to patients and their families, and has also created enormous labor and economic losses and even social problems such as serious employment. The goal of chronic hepatitis B treatment is to inhibit HBV replication before significant liver damage occurs. Currently, the international clinical guidelines for anti-HBV drugs include interferon (IFN) and nucleoside analogues, which are immune regulator and HBV DNA polymerase inhibitor, respectively. Both drugs have some effects, but also have shortcomings. INF has severe side effects, and most patients cannot tolerate. Nucleoside analogues require long-term use, and their long-term safety is unknown. In addition, nucleoside analogues cannot effectively eliminate HBV cccDNA (covalently closed circular DNA). There is drug resistance and relapse. Thus, existing antiviral drugs have some defects, so the complete clearance of HBV and cure caused by chronic Hepatitis B is still difficult to achieve. In the process of HBV replication, nucleotides play a very important role as a raw material for the synthesis and replication of HBV DNA, and the sugar metabolites intermediate ribose-5-phosphate is the raw material of nucleotides, so the glucose metabolism process is involved in the HBV DNA synthesis and replication process. AKT is a key regulatory factor in the process of glucose metabolism.

AKT (i.e., protein kinase B or PKB), which was originally thought to be isolated from AKR murine T-cell lymphoma in 1987, is a human homologue of the retrovirus AKT8 virus oncogene. The structure of AKT includes a PH site, a central kinase site and a hydrophobic HM regulatory site at the amino terminus, and the main phosphorylation sites are T308 and S473. AKT plays an important role in cell survival, growth, migration, migration, polarity, metabolism, cell cycle progression, skeletal muscle and myocardial contractility, angiogenesis, and stem cell self-renewal. mTOR (mammalian target of rapamycin) protein is a family member of phosphoinositide 3 kinase-related kinase, which integrates various extracellular signals such as nutrition, energy and growth factor, participates in biological processes such as gene transcription, protein translation and ribosome synthesis, and plays an important role in cell growth and apoptosis. mTOR has two complex forms, namely mTORC1 (mTOR complex 1) and mTORC2. mTOR is a downstream protein of AKT. After activation of AKT, it phosphorylates TSC2 and inhibits the formation of TSC½ complex, thus releasing the inhibition of Rheb and activating mTORC1. At the same time, AKT can directly phosphorylate PRAS40, thereby reducing the negative regulation of PRAS40 in mTORC1, and enhancing the activity of mTORC1. mTORC2 complex activates AKT by phosphorylation of the AKT-s473 site. Recent study indicates that these two proteins can lead to various diseases such as cancer, diabetes, cardiovascular disease, inflammatory diseases, fibrotic diseases, pulmonary hypertension, aging, neurodegenerative diseases, epilepsy, mental retardation, autism, but there are few reports of AKT and mTOR related to HBV.

SUMMARY OF THE INVENTION

The inventors discovered that AKT and mTOR had a certain effect on the replication of HBV DNA and HBV cccDNA in the study of the relationship of AKT and mTOR with HBV DNA and HBV cccDNA replication. When AKT and mTOR phosphorylation is increased, the level of HBV DNA in cells is also increased. The reason is that HBV DNA and cccDNA synthesis requires nucleotides as raw materials, and AKT and mTOR can affect the metabolic pathway of glucose, promote the synthesis of ribose-5-phosphate, and thus promote the synthesis of HBV DNA and cccDNA. This indicates that AKT and mTOR proteins can be used as new targets for anti-HBV therapy. The inhibition of these two proteins can eliminate not HBV DNA but also HBV cccDNA, thus creating a new and effective treatment for the complete elimination of HBV or other viruses.

The present invention relates to the treatment of Hepatitis B, specifically the difficulty to eliminate HBV cccDNA, resistance appeared during treatment, and relapse, and provides a new drug target to treat HBV by eliminating HBV cccDNA and an application for preparing a medicament for the treatment of Hepatitis B Virus.

To achieve the above goals, one technical aspect of the present invention is that a target for treating Hepatitis B Virus is AKT or mTOR.

The use of the AKT or mTOR target in the preparation of a medicament for the treatment of Hepatitis B Virus is to inhibit the synthesis of ribose-5-phosphate and HBV DNA and HBV cccDNA by inhibiting the activity of AKT and/or mTOR to inhibit.

In particular, the medicament that inhibit the activity of AKT or/and mTOR can be ADZ5363, AKTi-½ or/and rapamycin.

In the present invention, the following experiments are carried out:

1. the Activation of AKT can be Promoted when Infected by HBV

The expression of AKT-S473 was screened in hepatocyte line LO2, HepG2, HepG2.215, Bel, SMMC-7721. The expression of AKT-S473 in HepG2.215 cells transfected with HBV gene was higher than that of other cell lines.

HepG2 cells and Huh7 cells were transfected with different quality pcDNA3.1 and HBV1.3 plasmids, respectively. The phosphorylation of AKT was observed. It was confirmed that the expression of AKT was increased when HBV was present.

The comparison nude mice infected HVB long term and normal nude mice indicates that the AKT activity in infected nude mice was significantly higher than that in normal nude mice.

The expression of AKT-S473 in the liver tissue of Hepatitis B patients was significantly higher than that of the normal control group without HBV infection.

2. HBV DNA Replication is Promoted when AKT is Activated

The activation of AKT leading to the increase of HBV DNA was confirmed by transfection of EGFP-NA-AKT, which was able to inhibit endogenous AKT activation and had no AKT activity itself, and EGFP-CA-AKT, which had continuous AKT activity, in HepG2.215 cells.

3. AKT Inhibitor's In Vitro Anti-HBV Effect

The effects of AKT inhibitors ADZ5363 and AKTi-½ and mTOR inhibitor rapamycin on the expression of HBV DNA, cccDNA, HBsAg, HBeAg in HepG2.215 cells were observed after treating the HepG2.215 cells with the inhibitors, and were compared with antiviral drug tenofovir for effectiveness.

4. AKT Inhibitor's In Vivo Anti-HBV Effect

In vivo experiments were carried out in nude mice model of chronic Hepatitis B by injecting the mice with pAAV-HBV1.2 plasmid. AKT inhibitors ADZ5363, AKTi-½ and mTOR inhibitor rapamycin were compared with tenofovir. The changes of HBsAg in the livers of mice and the HBV DNA in the mouse blood after different treatment time were compared with those before treatment, and the anti-HBV effects of the inhibitors were compared with that of antiviral drug tenofovir.

AKT is activated when one is infected with HVB, and activated AKT prompts the replication of HBV. AKT and mTOR protein can be used as a new target for anti-HBV therapy. AKT and mTOR inhibitors not only have better antiviral effects than nucleoside analogues, e.g., tenofovir, but also reduce and clear HBV cccDNA. This solves the shortcomings of existing antiviral drugs that cccDNA cannot eliminated and relapse occurs, and has a very wide range of medical applications.

DETAILED DESCRIPTION OF THE ILLUSTRATED EMBODIMENTS

Figure 1:
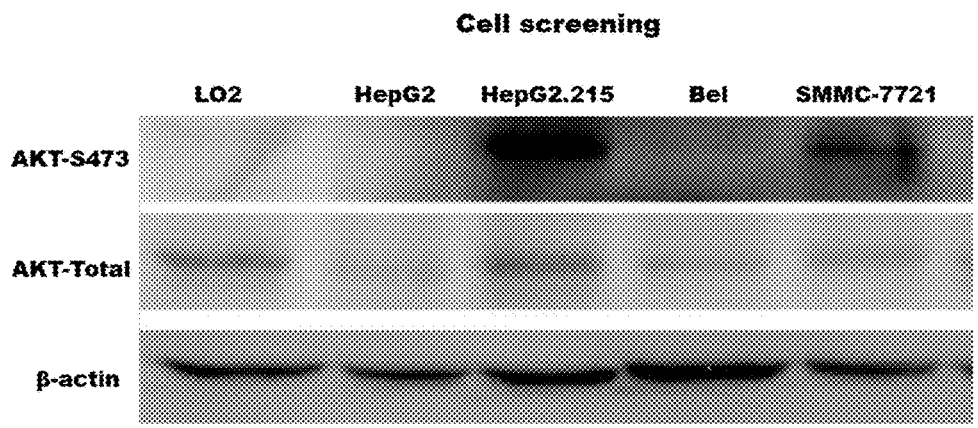
FIG. 1 shows the expression of AKT-Ser473 in hepatocytes LO2, HepG2, HepG2.215, Bel, and SMMIC-7721. The results showed that the expression of AKT-Ser473 in HepG2.215 transfected with HBV gene was higher than that in other cells, indicating that the activation of AKT is prompted when cells were infected with HBV.

1. The expression of AKT-Ser473 in LO2, HepG2, HepG2.215, Bel, SMMC-7721 cells was detected by western blot. The results showed that AKT-Ser473 in HepG2.215 cells was higher than that in other cells. FIG. 1 shows that HBV infection can promote the activation of AKT.

Figure 2:
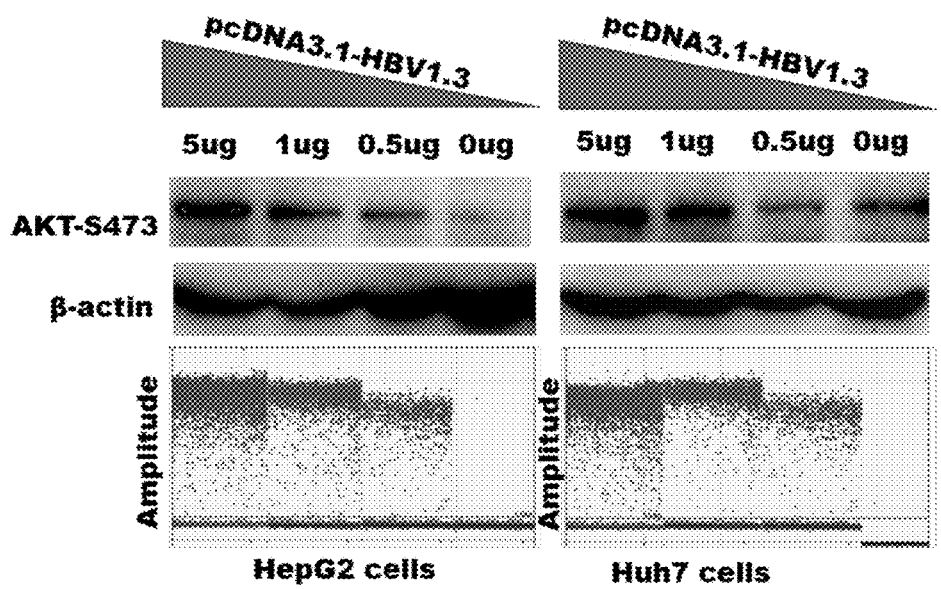
FIG. 2 shows HepG2 cells and Huh7 cells transfected with different quality pcDNA3.1-HBV1.3 plasmid and AKT phosphorylation changes.

2. HepG2.215 cells were placed in a 6-well plate at a density of $8 \times 10^6$ per well. 10 μL Lipo2000 was dissolved in 100 μL opto-MEM (gibico) medium and placed for 5 minutes. 5 μg, 1 μg, and 0.5 μg pcDNA3.1-HBV1.3 plasmid were dissolved in 100 μL opti-MEM, respectively, and the plasmid solutions were then added to lipo2000, and placed at room temperature for 15 minutes. Finally, 5 μg, 1 μg, and 0.5 μg of the HNV plasmid were added to HepG2 and Huh7 cells, respectively. After 48 hours, cell protein was extracted for western blot analysis, and the cell culture supernatant was collected and extract for DNA for digital PCR. The changes of AKT phosphorylation and HBV DNA were recorded. See FIG. 2. The results showed that when normal cells were transferred with the virus plasmid, AKT activity was increased, indicating that HBV replication and AKT are related.

3. (1) Building nude mice model long-term infected with HBV

① Each nude mouse was injected with 6 μg plasmid dissolved in 2 mL PBS at room temperature, materials, plasmids, and mice were transported to the animal room.

② The nude mice were 8 weeks old and fixed on lab bench for weighing. Each mouse was about 20 mg.

③ The nude mice were irradiated with 200-watt light bulb until blood vessels were expended and bodies turned red. The nude mice were placed in a fixed device. Tail veins were cleaned with alcohol cotton balls, blood vessels were expanded, and both sides of the tail veins ⅔ from the end of the root were chosen for injection.

④ 2 mL PBS (including 6 μg plasmid) 5 s was injected into the mice.

⑤ 3 weeks after the injection, the tip of the mouse tail was cut to collect 100 μL anti-coagulated whole blood, and 1.75 μL sodium citrate anticoagulant (citrate 0.48 g, sodium citrate 1.32 g, glucose 1.47 g, adding water to 100 mL) was added to the blood. The blood was then placed in a 1.5 mL centrifuge tube.

3. (2) Immunohistochemistry used to detect the expression of AKT-s473 and HBsAg proteins in liver tissue ① Liver tissue was fixed with 40 g/L paraformaldehyde at 4° C. for 30 min.

② Preparation of paraffin sections, cutting conventional slices, dewaxing: 30 mL/L $H_2O_2$ inactivation of endogenous peroxidase, 50 g/L BSA room temperature sealed for 20 min.

③ Rabbit anti-AKS-s473 (1:200) and rabbit anti-HBsAg antibody (1:200) were incubated overnight at 4° C. After washing, biotinylated goat anti-rabbit IgG (1:100) was added, 37° C., 2 h.

Figure 3:
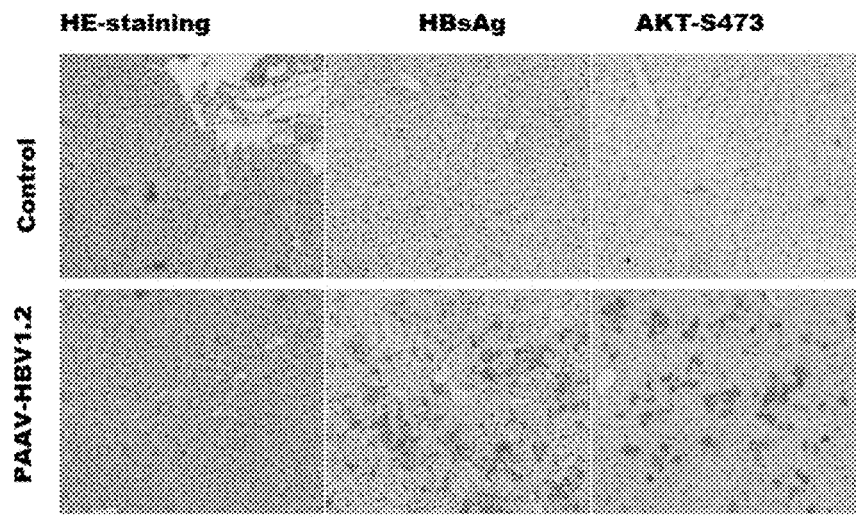
FIG. 3 shows the expression of AKT in liver tissue of nude mice infected with HBV and normal nude mice

④ Alkaline phosphatase-labeled streptavidin was added, 37° C., 20 min. 5-bromo-4-chloro-3-indolyl phosphate/nitrogen blue tetrazolium mixture (BCIP/NBT) (1:20) coloring 20 min, nuclei solid red re-coloring, observation after sealing. See FIG. 3.

The results showed that the expression of AKT-Ser473 in HBV-carrying nude mice was higher than that in normal nude mice, which indicated that HBV infection could promote the activation of AKT.

Figure 4:
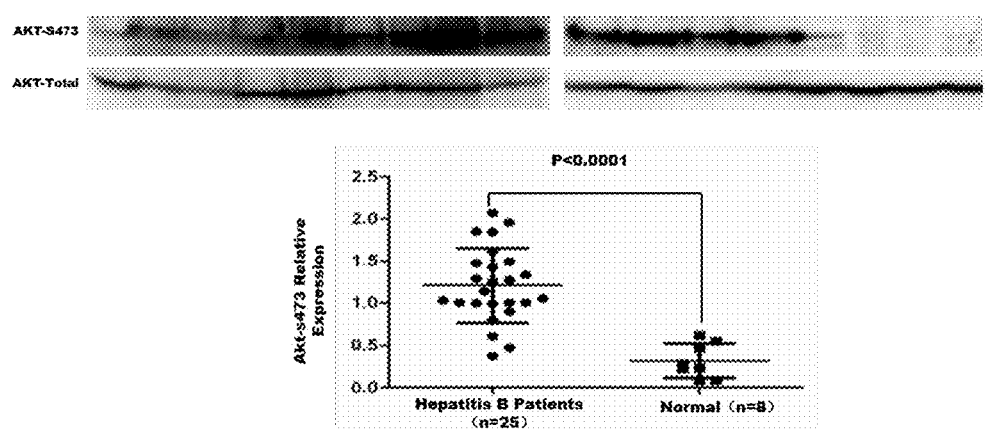
FIG. 4 shows the difference of AKT activation levels in liver tissue of patient infected with HBV and normal person.

4. The liver tissue samples of 25 patients with chronic hepatitis B and the liver tissue samples of 8 patients without HBV infection were examined by western blot. The results showed that the expression of AKT-S473 in hepatocytes of patients with chronic hepatitis B was significantly higher than that of patients without HBV infection. See FIG. 4. This indicated that HBV infection could promote the activation of AKT.

Figure 5:
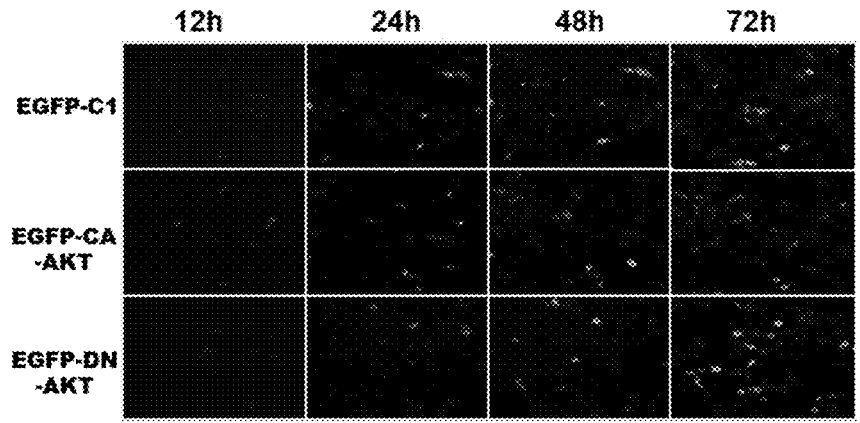
FIG. 5 shows the change of HBV DNA after transfection of EGFP-NA-AKT plasmid, which was able to inhibit endogenous AKT activation and had no AKT activity itself, and EGFP-CA-AKT plasmid, which had continuous AKT activity, in HepG2.215 cells.
Figure 5:
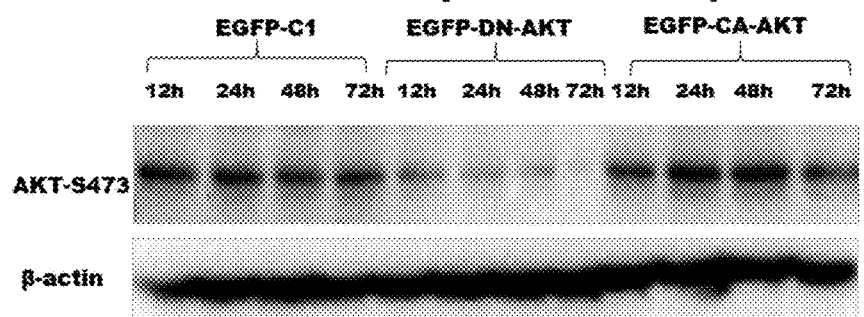
Figure 5:
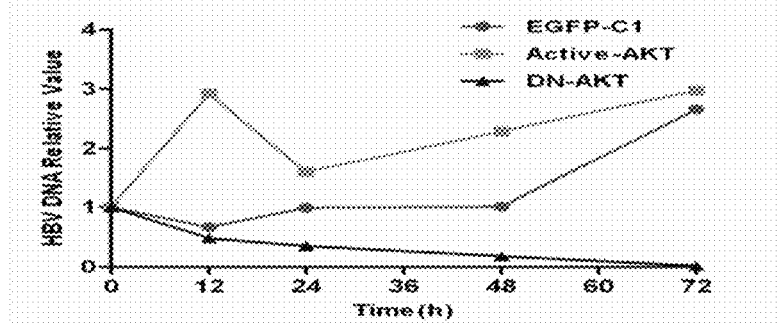

And at 0 h, 12 h, 24 h, 48 h, 72 h, respectively, from the time of transfection, 5. HepG2.215 cells were plated in a 6-well plate at a density of $8 \times 10^6$ per well. Lipo200010u was dissolved in 100 μL opto-MEM (gibico) medium and set for 5 min. 4 μg EGFP-NA-AKT and EGFP-CA-AKT plasmids were dissolved in 100 μL opti-MEM, respectively. EGFP-NA-AKT and EGFP-CA-AKT plasmids were added to lipo2000, incubated at room temperature for 15 min, and finally added to hepg2.215 cells. At 0 h, 12 h, 24 h, 48 h, 72 h after transfection, the fluorescence of the cells was record (FIG. 5a). The cell culture supernatant was collected and HBV DNA was extracted for digital PCR to observe the changes of HBV (FIG. 5c). The results showed that after HepG2.215 cells were transfected with plasmids that can activate and inhibit AKT, the inhibition of ATK decreased HBV DNA, which indicated the decrease the content of HBV DNA was related to the inhibition of AKT activation.

6. ADZ5363, AKTi-½, rapamycin (RAPA) anti-HBV DNA dose and the drug-resistant drug tenofovir (TDF) comparison:

(1) Different doses of RAPA (10 μM, 0.5 μM, 1 μM), ADZ5363 (10 nM, 100 nM, 1000 nM), AKTi½ (10 nM, 100 nM, 1000 nM) and TDF (0.1 μM, 0.15 μM, 0.25 ΞM, 1 μM) were added to HepG2.215 medium; continuous dosing for three days, adding additional dose every 24 hours, and the supernatants of the cells were collected after 3 days.

(2) Extraction of HBV DNA supernatant: 500 μL HepG2.215 cell suspension was centrifugation at 4° C. at 5000 r/min for 15 min; the precipitation discarded; and the supernatant was collected. Treatment of the supernatant: 0.5% SDS+10 mmol TRIS-HCL (pH 8.0)+0.1 mol EDTA (pH 8.0) was added, followed by 100 μg/mL proteinase K, at 56° C. water bath for 1 h. The supernatant was collected and added an equal volume of tris saturated phenol 650 μL (up and down thoroughly mixed), centrifuged (4° C., 12000 r/min, 10 min). After centrifugation, 600 μL upper layer of water was collected and added an equal volume of phenol:chloroform:isoamyl alcohol (25:24:1) 600 μL, up and down thoroughly mixed, set at room temperature for 10 min, centrifuged (4° C., 12000 r/min, 10 min). After centrifugation, 500 μL upper layer of water was collected, and added 4° C. pre-cooled ¹/₁₀ volume of sodium acetate 50 μL (3 mol/L, pH=5.2), and 2 times the volume of anhydrous ethanol (4° C. precooling) 1.1 mL, up and down thoroughly mixed, set at −20° C. for 10 min, centrifuged (4° C., 12000 r/min, 10 min). The supernatant was discarded, and 1 mL 70% ethanol was added, washed twice, centrifuged (4° C., 12000 r/min, 10 min). The remaining ethanol was removed (about 30 min), and double distilled water 40 μL was added.

Figure 6:
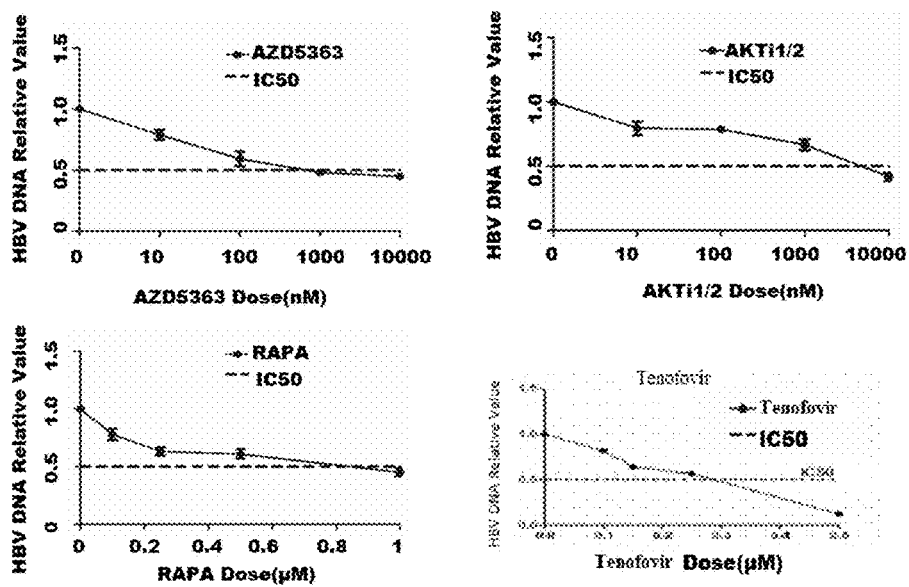
FIG. 6 shows the effect of different doses of ADZ5363, AKTi-½, rapamycin on HBV DNA in HepG2.215 cells and their antiviral effects compared with tenofovir.

(3) HBV DNA content in supernatant was detected by digital PCR. The results of the comparison are shown in FIG. 6. It indicated that AKT and mTOR inhibitors can effectively reduce the effect of HBV DNA and the antiviral effect is better than TDF.

7. The effect of treating HepG2.215 cells with ADZ5363, AKTi-½, and rapamycin at different times on HBV DNA, cccDNA, HBsAg, HBeAg (1) The concentrations of ADZ5363, AKTi-½, rapamycin were 1 Um, and 6 time points were set, 0 day, 3 days, 6 days, 9 days, 12 days and 15 days. hepg2 .2.15 cells in the number of 1.5×10⁶ cells were placed. Each time point corresponds to a 6 cm cell culture dish.

After overnight adhere, 15-day drug treatment cells were added a specific concentration of drugs. After 24 hours, the 15-day drug treatment cells were added the drugs. After 3 days, the 15-day drug treatment cells and 13-day drug treatment cells were added the drugs. The drugs were administered in this manner for 15 days. After all the drugs were added, the supernatant of cells was collected.

(2) The collection of the supernatant of HBV DNA: the same method as above.

Figure 7:
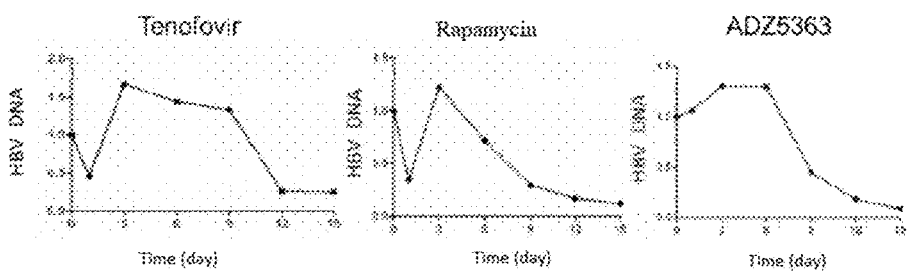
FIG. 7 shows HepG2.215 cells in ADZ5363, rapamycin treatment with the treatment time after the extension of HBV DNA changes and the efficacy of tenofovir antivirus comparison.
Figure 8:
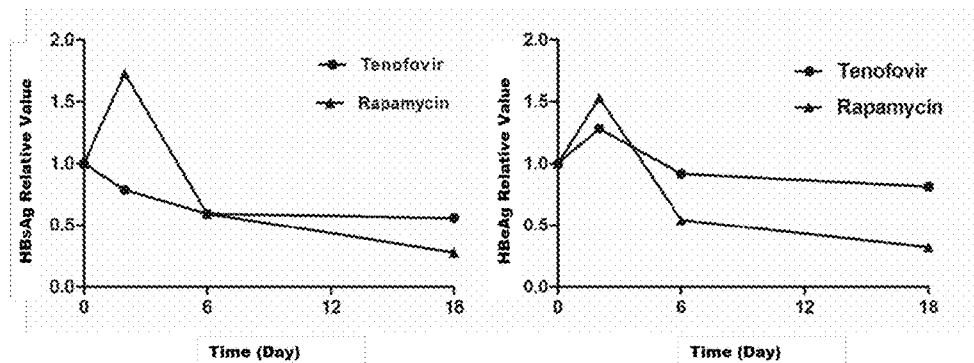
FIG. 8 shows the HBsAg and HBeAg changes in HepG2.215 cells after treatment with rapamycin compared with tenofovir.

(3) The detection of HBV DNA content with digital PCR: the same method as above. See FIG. 7.

(4) The detection of the changes HBsAg, HBeAg with clinical methods. See.

Figure 9:
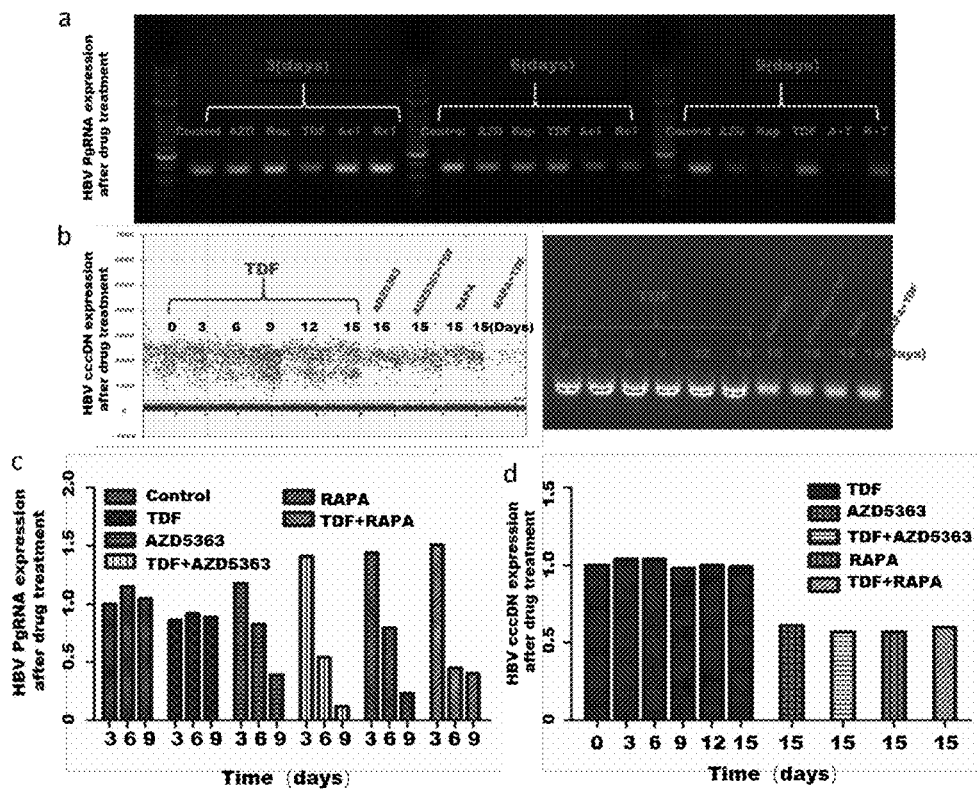
FIG. 9 shows the changes of HBV cccDNA in HepG2.215 cells after ADZ5363 and rapamycin treatment.

(5) The detection of cccDNA with a regular semi-quantitative method. See FIG. 9.

Extraction of HBV cccDNA:

The supernatant was treated with a mixture 150 mmol/L NaCl, 50 mmol/L Tris-HCl (pH 7.4), 10 mmol/L EDTA, 0.1% SDS Proteinase K (800 μg/mL) was set at 37° C. overnight. Same volume of tris saturated phenol 500 was added to the mixture, and up and down thoroughly mixed, then centrifuged (4° C., 12000 r/min, 10 min). 500 μL of upper water layer was collected and added same volume 500 μL of phenol:chloroform:isoamyl alcohol (25:24:1), up and down thoroughly mixed, set at room temperature for 10 min, centrifugation (4° C., 12000 r/min, 10 min).

After centrifugation, 450 μL upper layer of water was collected, and added 4° C. pre-cooled ¹/₁₀ volume of sodium acetate 45 μL (3 mol/L, pH=5.2), and 2 times the volume of anhydrous ethanol (4° C. precooling) 1.1 mL, up and down thoroughly mixed, set at −20° C. for 10 min, centrifuged (4° C., 12000 r/min, 10 min). The supernatant was discarded, and 1 mL 70% ethanol was added, washed twice, centrifuged (4° C., 12000 r/min, 10 min). The remaining ethanol was removed (about 30 min), and TE buffer 40 μL was added, and frozen for future use.

Primer Design and Synthesis:

The primers were synthesized by a biological company, and the sequences re as follows:

```
P1-
                                    (SEQ ID NO. 1)
5'CTGAATCCTGCGGACGACCC (nt 1443-1462)

P2-
                                    (SEQ ID NO. 2)
5'GCCCCAAAGCCACCCAAG (nt 1885-1902)
```

Closed Loop DNA Safe DNA Enzyme Purification:

Digestion system: 3 μg DNA, 5 μL 10× buffer, 2 μL 25 mMATP, 10U DNase, adding ddH₂O to 50 μL, keeping at 37° C. constant temperature for 30 min. 70° C. constant temperature for 30 min inactivated the enzyme.

PCR Amplification:

Reaction system: 1 μL 10 um P1, 1 μL 10 um P2, 2×taqPCRMsterMix 10 μL, adding ddH₂O to 20 μL.

Reaction conditions: 95° C. preheat 1 min, 95° C. 10 s, 58° C. 5 s, 63° C. 15 s, 72° C. 20 s, 34 cycles.

The results showed that HBV DNA, HBsAg, HBeAg and cccDNA were significantly decreased with the increase of target inhibitor time, and the effect was better than that of antiviral drug telenovir.

Agarose Gel Electrophoresis

8. Nude mice with chronic hepatitis B model before and after treatment of HBV DNA changes.

Nude mice model with long-term HBV long-term was prepared by the same way as above. Based on drugs tested, mice were divided into ADZ5363 (10 mg/kg/day) treatment group, TDF (300 mg kg/day) treatment group, ADZ5363 (10 mg/kg/day) and TDF (300 mg kg/day) combined treatment group, and control (no drug treatment) group. Mice were treated with the above doses for 4 weeks.

Figure 10:
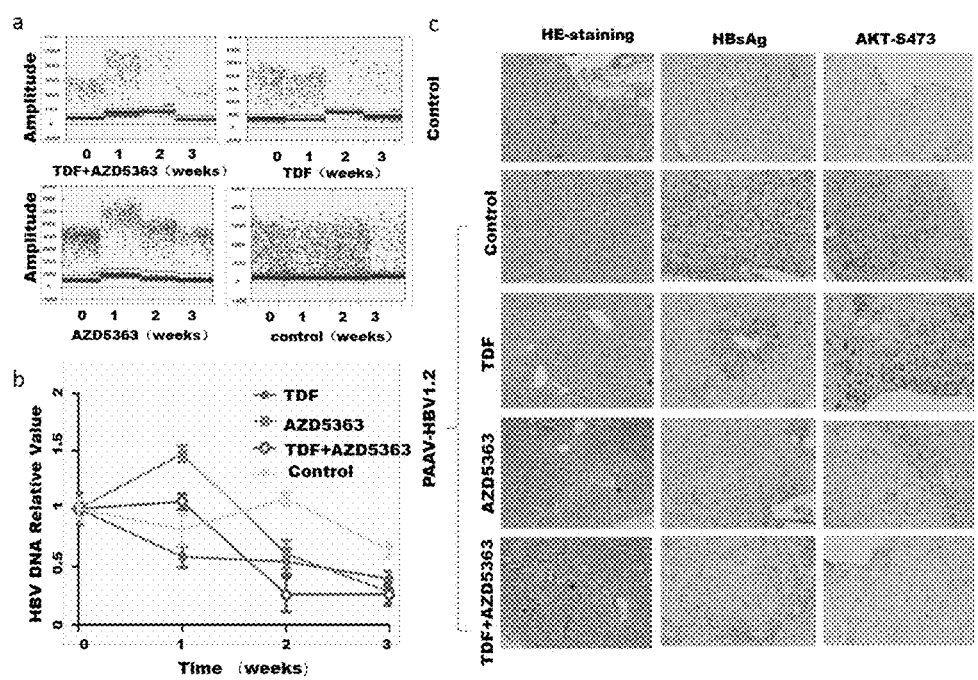
FIG. 10 shows the changes of HBV DNA in nude mice infected with HBV before and after treatment.

Each week, the tails of the mice were cut to collect blood samples. Blood DNA was extracted with DNeasy® Blood & Tissue blood extraction kit. HBV DNA was quantitatively detected by ddPCR. See FIG. 10.

One month after drug treatment, mouse liver was collected. The changes of AKT-S473 and HBsAg in the liver after drug treatment were detected by immunohistochemistry (in the same manner as above). See FIG. 10.

The results of in vivo experiments show that AKT inhibitors have anti-HBV effects and can reduce HBsAg.

What is claimed is:

1. A method of treating a patient with hepatitis B virus (HBV) infection comprising: inhibiting the activities of AKT by administering ADZ5363 to the patient, wherein said administration inhibits the synthesis of 5-phosphate ribose and HBV DNA and HBV cccDNA.

2. The method of claim 1, wherein the method further comprises administering rapamycin to the patient to inhibit the activities of mTOR simultaneously.

* * * * *